United States Patent [19]
Wheelwright et al.

[11] Patent Number: 6,114,379
[45] Date of Patent: Sep. 5, 2000

[54] BIOAVAILABLE CHELATES OF CREATINE AND ESSENTIAL METALS

[75] Inventors: David C. Wheelwright; Stephen D. Ashmead, both of Clearfield, Utah

[73] Assignee: Albion Laboratories, Inc., Clearfield, Utah

[21] Appl. No.: 09/348,359

[22] Filed: Jul. 7, 1999

[51] Int. Cl.$^7$ .......................... A61K 31/28; C07F 13/00; C07F 11/00; C07F 15/00; C07F 1/00

[52] U.S. Cl. .......................... 514/492; 514/499; 514/501; 514/502; 514/505; 556/50; 556/63; 556/116; 556/134; 556/148; 562/899

[58] Field of Search .................. 556/50, 63, 116, 556/134, 148; 562/899; 514/492, 499, 501, 502, 505

[56] References Cited

U.S. PATENT DOCUMENTS

| | | | |
|---|---|---|---|
| 4,020,158 | 4/1977 | Ashmead et al. | 424/177 |
| 4,167,564 | 9/1979 | Jensen | 424/177 |
| 4,216,143 | 8/1980 | Ashmead | 260/113 |
| 4,216,144 | 8/1980 | Ashmead | 260/115 |
| 4,599,152 | 7/1986 | Ashmead | 204/72 |
| 4,725,427 | 2/1988 | Ashmead et al. | 424/44 |
| 4,774,089 | 9/1988 | Ashmead | 424/157 |
| 4,830,716 | 5/1989 | Ahsmead | 204/72 |
| 4,863,898 | 9/1989 | Ashmead et al. | 514/6 |
| 5,162,369 | 11/1992 | Ashmead et al. | 514/492 |
| 5,397,786 | 3/1995 | Simone | 514/300 |
| 5,576,316 | 11/1996 | Cohn | 514/218 |
| 5,888,553 | 3/1999 | Grant et al. | 424/655 |

*Primary Examiner*—Porfirio Nazario-Gonzalez
*Attorney, Agent, or Firm*—Thorpe, North & Western, LLP

[57] ABSTRACT

A chelate comprised of creatine bonded to an essential mineral selected from the group consisting of Mg, Ca, Cu, Zn, Fe, Cr, Co, Mo, Se and Mn to form a heterocyclic ring. Preferably, the metal is Mg, but Ca, Zn, Fe, Cr and Mn are also preferred. The creatine chelates of the present invention are capable of being absorbed in the stomach or intestines via active transport without substantial metabolism of the chelate. In other words, the creatine ligand is protected by the metal from undergoing cyclization in the acidic environment of the stomach and the metal is made more bioavailable due to the presence of the creatine ligand.

54 Claims, No Drawings

BIOAVAILABLE CHELATES OF CREATINE AND ESSENTIAL METALS

FIELD OF THE INVENTION

The present invention relates to a chelate comprised of creatine and various essential metals selected from the group consisting of Mg, Ca, Cu, Zn, Fe, Cr, Co, Mo, Se and Mn, preferably Mg. These chelates are absorbed into biological tissue and subsequently migrate to specific tissue sites where the various chelates are utilized by corresponding tissue. The respective tissue sites may have use for the chelates intact as delivered or as dissociated chelates in the form of a mineral cation and/or creatine.

BACKGROUND OF THE INVENTION

When a metal combines with an electron donor ligand, a complex or coordination compound is formed. Further, when an electron donor contains two or more donor groups tied together in some way, the ligand is referred to as a polydentate ligand, e.g., a bidentate ligand has two donor groups. The commonality found in all chelates is the formation of a heterocyclic ring comprised of a ligand and a metal atom. For ring formation to occur, several conditions must be present. First, the electron donor molecule must contain two or more groups that can each combine with a particular metal atom. Second, groups and/or atoms must be present that can simultaneously coordinate with the metal atom through their electron pairs. Finally, these donor groups must be separated from each other by sufficient atoms so that sterically permissible heterocyclic rings may be formed. An example of a chelate involving two organic ligands, each ligand containing a carboxyl functional group and an α-amine functional group, may be depicted by the following graphic:

FORMULA 1

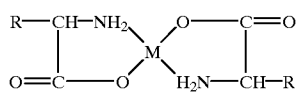

In the above depiction, M represents the metal atom that acts as the closing member for the organic ligands.

The structure, chemistry and bioavailability of amino acid chelates are well documented, e.g. Ashmead et al., *Chelated Mineral Nutrition*, (1982), Chas. C. Thomas Publishers, Springfield, Ill.; Ashmead et al., *Intestinal Absorption of Metal Ions*, (1985), Chas. C. Thomas Publishers, Springfield, Illinois; Ashmead et al., *Foliar Feeding of Plants with Amino Acid Chelates*, (1986), Noyes Publications, Park Ridge, N.J.; U.S. Pat. Nos. 4,020,158; 4,167,564; 4,216,143; 4,216,144; 4,599,152; 4,774,089; 4,830,716; 4,863,898 among others.

Additionally, flavored effervescent mixtures of vitamins and amino acid chelates in the form of a beverage have also been disclosed in U.S. Pat. No. 4,725,427.

In the field of mineral nutrition, amino acid chelates have increasingly been recognized as providing certain advantages over inorganic mineral salts. One advantage is attributed to the fact that these chelates are readily absorbed in the intestines via mucosal cells by means of active transport as though they were small peptides. In other words, the minerals are absorbed along with the amino acids as a single unit by utilizing the amino acids as carrier molecules. This method of metal absorption is beneficial because it enables absorption of specific metals into the body without utilizing standard absorption sites for free metal ions. Therefore, the problems associated with the competition of ions for active sites and the suppression of specific nutritive mineral elements by others are avoided. Other advantages of amino acid chelates include stimulation of gonadotropic hormones as is disclosed in U.S. Pat. No. 4,774,089, delivery of metal ions to targeted tissue sites disclosed in U.S. Pat. No. 4,863,898 and enhancement of the immune system disclosed in U.S. Pat. No. 5,162,369.

Creatine, also known as N-(Aminoiminomethyl)-N-methylglycine, methylglycoamine or N-methyl-guanido acetic acid is a well known substance. In fact, creatine is listed in *The Merck Index*, Twelfth Edition, No. 2637, and may be represented as follows:

FORMULA 2

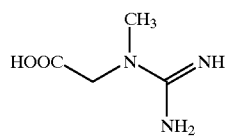

It is important to note that creatine is susceptible to cyclization. Perhaps, because of the positioning of the $NH_2$ gamma to the carboxylic acid, creatine is labile to acid hydrolysis. Regardless of any purported rational, under acidic conditions, creatine has the propensity to form creatinine, which may be represented by the following formula:

FORMULA 3

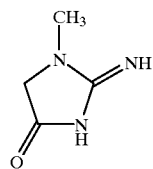

In fact, in acidic aqueous solutions, the formation of creatinine from creatine is nearly quantitative and irreversible. Cannan, Shore, *Biochem. J.* 22, 924 (1928). With this in mind, it is apparent that the exposure of creatine to the acidic environment of the stomach will cause an irreversible formation of creatinine. Once creatinine is formed, any further biological use of ingested creatine will be precluded.

Muscle contraction and relaxation are fueled by energy liberated during the dephosphorylation of adenosinetriphosphate (ATP). The ATP stored within a cell is rapidly depleted during even normal activity. For normal tissue function to continue, ATP must be rapidly resynthesized from its breakdown products, one of which is adenosinediphosphate (ADP). During maximal exercise of a short duration, this resynthesis is accomplished almost exclusively by the anaerobic degradation of phosphocreatine (PCR) and glycogen. Hultman E. et al., *Energy metabolism and fatigue*; Taylor A. et al., eds. *Biochemistry of exercise VII*, Champaign, Ill., Human Kinetic Publishers, 1990: vol. 21, 73–92. It has also been proposed that the observed decline in force production during intense muscle contraction may be related to the availability of muscle PCR stores. Greenhaff P. L. et al., *Influence of oral creatine supplementation of muscle torque during repeated bouts of maximal voluntary exercise in man, Clinical Science* (1993) 84, 565–571. The depletion of these PCR stores limits the rephosphorylation of ADP, thereby limiting the ATP available for energy production. Greenhaff further proposed that any mechanism capable of increasing the total intramuscular creatine store might arrest PCR depletion during intense muscular contraction and offset, or even prevent, the decline in the rate of ADP rephosphorylation during exercise. However, no efforts were made to explain the increase of creatine within the muscle cells. Greenhaff merely relied upon work previously published that demonstrated that the creatine content of skeletal muscles could be increased by 20%–50% through standard oral pathways. However, in that study, in order to achieve this marginal increase in the creatine content of muscle cells, the subjects of the study were required to ingest 20 grams of creatine hydrochloride. Harris R. C. et al., *Elevation of creatine in resting and exercised muscle of normal subjects by creatine supplementation*, Clin. Sci., 1992; 83: 367–74.

Creatine can be found biologically in diverse portions of the body. However, some reports indicate that creatine is found primarily in the nerves and muscle. Walker J. B., *Creatine: Biosynthesis, regulation, and function; Adv. Enzymology and Related Areas of Molecular Biology* (1979) 50: 177–242. Essentially, creatine is used biologically for the regeneration of ATP from ADP. However, in the process of regenerating ATP, creatine is irreversibly transformed to creatinine which in turn, is eliminated from the body through the urine. Because creatine is irreversibly used, i.e., from creatine to creatinine, the body must either produce creatine biochemically or secure an outside source to supply the body with needed creatine.

Biochemically, the human liver and pancreas use various amino acids such as glycine, serine, arginine and methionine to synthesize creatine. However, when sufficient in one's diet, creatine may be made bioavailable through ingestion. Although animal muscle contains approximately 0.5% creatine by weight, most of the creatine which is bioavailable for ingestion is degraded by the cooking process. Therefore, cooked meat is a poor source of ingestible creatine. Moreover, plants and/or vegetables are also a poor source of creatine.

The securing of creatine from an outside source has also been discussed in several recent U.S. patents. U.S. Pat. No. 5,397,786 entitled, REHYDRATION DRINK, discloses a drink for the treatment and prevention of the loss of essential electrolytes due to fluid loss. This patent teaches that creatine, B vitamins, pantothenic acid and choline are energy enhancers. Additionally, this invention provides for the addition of numerous salts such as $MgCO_3$, $CaCO_3$ and magnesium aspartate as supplements containing essential nutrients. Although the necessity of these elements in a healthy metabolism was recognized, the use of ionic salts is largely ineffective because most of the ingested elements are lost in the acidic environment of the stomach.

U.S. Pat. No. 5,576,316 entitled METHOD FOR INHIBITING TUMOR GROWTH RATE USING CREATINE OR CREATINE ANALOGS discloses the use of creatine and creatine analogs for the treatment of tumors. Specifically, this invention teaches that the administration of creatine in the form of a salt can reduce a tumor's growth rate. The patent further teaches that significant portions of orally administered creatine are lost through the urine without having been used by the body at all.

Finally, U.S. Pat. No. 5,888,553 entitled NON-STEROIDAL ANABOLIC COMPOSITION discloses a composition used to build and sustain muscle mass. The complex is comprised of effective amounts of chromium salt and a magnesium glycyl glutaminate chelate as core ingredients. Optional ingredients include a magnesium amino acid chelate, an α-glutaric acid salt of ornithine, creatine (or a salt thereof) and a branched chain amino acid (leucine, isoleucine and/or valine).

Based upon what is known about the prior art, there is a need to provide a composition and method of making a compound that enables creatine and essential metals to be introduced to the body in such a manner so that more creatine than previously known in the art may be used by the body prior to undergoing cyclization. In other words, it would be desirable to provide a creatine chelate for oral consumption comprised in such a way that the creatine ligand is protected by the metal from undergoing cyclization in the acidic environment of the stomach, thus making the creatine more readily available to the body in a useful form. Further, it would be desirable to provide a creatine chelate so that the metal is made more bioavailable due to the presence of the creatine ligand.

OBJECTS AND SUMMARY OF THE INVENTION

It is an object of the present invention to provide a creatine chelate composition which, when ingested into a living organism, will be transported to one or more sites within the organism such as muscle, nerve, brain tissue, enzyme system, immune system, blood cells or tumors.

It is another object of the present invention to provide a nutrient formulation which enhances fatigue resistance and recovery time during high intensity, short-term exercise by providing a nutrient formulation which is comprised of the anabolic nutrients phosphorus and creatine, which are precursors for the bodies formation of phosphocreatine.

It is another object of the present invention to complement creatine and phosphorus with chelated magnesium as an activator of the enzymes that hydrolyze and transfer phosphate groups, e.g. the phosphatases and those concerned in the reactions involving adenosine triphosphate (ATP).

It is another object of the present invention is to provide a creatine chelate for oral consumption such that the chelate remains intact in the acidic conditions of the stomach, thereby providing a mechanism to prevent creatine from undergoing cyclization before it reaches the target tissue.

It is yet another object of the present invention is to provide a metal selected from the group consisting of Mg, Ca, Cu, Zn, Fe, Cr, Co, Mo, Se and Mn in a form that has enhanced bioavailability over inorganic salts.

These and other objects may be accomplished by providing a creatine chelate composition and method for making and using the same. Creatine chelates may be absorbed through the intestinal tract as intact molecules, and subsequently, may then be transported to various tissues for use as intact chelates, creatine and/or metal ions. This is possible because these chelates are protected from dipeptidase activity due to the presence of metal. Further, they are also protected from acid hydrolysis because the hydrolysis reaction of a creatine chelate is energetically disfavored.

DETAILED DESCRIPTION OF THE INVENTION

Before the present invention comprising a creatine chelate and method of making the same is disclosed and described, it is to be understood that this invention is not limited to the particular process steps and materials disclosed herein as such process steps and materials may vary to some degree. It is also to be understood that the terminology used herein is used for the purpose of describing particular embodiments only and is not intended to be limiting as the scope of the present invention will be limited only by the appended claims and equivalents thereof.

It must be noted that, as used in this specification and the appended claims, singular forms of "a," "an," and "the" include plural referents unless the content clearly dictates otherwise.

"Bioavailable" means, for purposes of this invention, that the creatine chelate, creatine and/or the metal is available to the body. In the case of creatine, the metal provides a mechanism of protecting the creatine from undergoing cyclization in the acidic environment of the stomach.

"Chelate" means, for purposes of this invention, that the creatine ligand forms a heterocyclic ring with the metal as the closing member. Coordinate covalent bonds may exist at both the carboxyl oxygen group and amine groups may exist. However, coordinate covalent bonds are not required as long as there is at least one bidentate ligand and a metal which interact to form a ring, i.e. coordination with the amine groups and coulombic attraction to the negatively charged carboxyl group.

With this in mind, the present invention is essentially a metal chelate comprising a creatine ligand bonded to a metal selected from the group consisting of Mg, Ca, Cu, Zn, Fe, Cr, Co, Mo, Se and Mn to form a chelate ring and having a ligand to metal molar ratio from about 1:1 to 3:1. The chelate is formed by reacting creatine with a metal under reaction conditions that are conductive to chelate formation. The creatine may be provided by a member selected from the group consisting of creatine, creatine salts, creatine esters, creatine amides and creatine hydrates. The metal may be provided by a member selected from the group consisting of magnesium (Mg), calcium (Ca), copper (Cu), zinc (Zn), iron (Fe), chromium (Cr), cobalt (Co), molybdenum (Mo), selenium (Se) and manganese (Mn) in elemental form or in the form of chlorides, sulfates, oxides, hydroxides, carbonates and/or bicarbonates. A preferred basic structure of a creatine chelate may be depicted as follows:

FORMULA 4

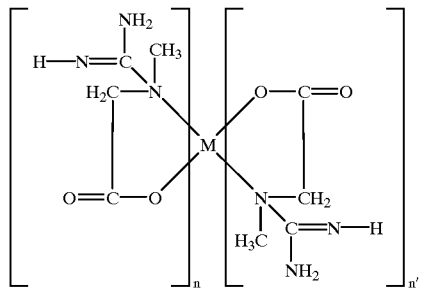

In the above depiction, M is a metal, n is 1 and n' is 0, 1, or 2. However, it is most preferred that n' is 0 providing a ligand to metal molar ratio of 1:1. To illustrate this aspect of the invention, magnesium creatine may have a ligand to metal molar ratio of 2:1 (n'=1), but 1:1 (n'=0) is preferred. Additionally, other preferred ligand to metal molar ratios include creatine to calcium at 1:1 (n'=0); creatine to zinc at 1:1 (n'=0); creatine to chromium at 1:1 (n'=0), 2:1 (n'=1) and/or 3:1 (n'=2); creatine to manganese at 1:1 (n'=0); and creatine to iron a 1:1 (n'=0), 2:1 (n'=1) and/or 3:1 (n'=2). When n'=0, there may be one or more anions present in the solution (see Formula 5 below). It is important to note that the bonds depicted between the metal (M) and the amine group and between the metal (M) and carboxyl oxygen group as shown and described should not necessarily be strictly construed to represent coordinate covalent bonds. For example, in one embodiment, a covalent bond may exists between the metal (M) and the amine group whereas an ionic or coulombic bond exists between the metal (M) and the carboxyl oxygen group (see Formula 6 below). However, for optimal absorption through the intestinal tract, the net electrical charge at the metal ion is preferably zero. In other words any positive charge on the metal ion is neutralized by electrons contributed by the ligand in formation of the heterocyclic chelate ring.

Generally, the method of preparing the creatine chelates of the present invention is as follows. First, a soluble metal salt or an insoluble metal compound is dissolved in water or solubilized in an acidic solution respectively. If an acidic solution is required to disassociate the metal ions, acids such as acetic, citric, lactic, malic, hydrochloric, phosphoric, sulfuric, tartaric, maleic and naturally occurring amino acids such as aminobutyric, aspartic and glutamic acids, etc., may be used. If a metal salt is used that is soluble in water, it may not be required to use an acidic solution, though it may be desired. To illustrate, if magnesium is the metal to be chelated, magnesium sulfate, magnesium citrate, magnesium chloride, magnesium phosphate monobasic, magnesium nitrate, magnesium oxide, etc., may be used as the metal source which will either be dissolved in water or acidified in an acidic solution. To this solution, a creatine ligand is then added. If the pH level is not around neutral, i.e., if it is between about 7.5 and 10, a pH adjuster may be added. pH adjusters may include o-phosphoric acid, citric acid, malic acid, acetic acid, hydrochloric acid, tartaric acid, lactic acid, nitric acid, sulfuric acid and naturally occurring amino acids such as aminobutyric acid, aspartic acid and glutamic acid among others, though o-phosphoric acid is preferred. For example if a creatine chelate is prepared by reacting a creatine ligand with a metal oxide in the presence of citric acid, o-phosphoric acid or another acidifying agent may be added to lower the pH from more basic levels (about 7.5 to 10) to a more neutral pH (about 7).

It is important to note t hat the order that one mixes the ingredients is not central to the invention. The creatine ligand may be added to the aqueous acidic solution first followed by the addition of the metal, or even simultaneously. However, these embodiments are not preferred because the creatine ligand may undergo hydrolysis, i.e., cyclization to creatinine, if exposed to the acidic environment for an extended period of time prior to the addition of the metal.

The product magnesium creatine, a preferred embodiment, may be prepared by reacting magnesium oxide, creatine, o-phosphoric acid and citric acid in an aqueous environment. The formulation is stoichiometrically balanced so that no unreacted magnesium oxide remains in the product. The product is believed to involve the interaction between the magnesium ion and the ligand creatine by coulombic attraction to the negatively charged carboxyl group and coordination with the amine group. Of the possible combinations and permutations, one possible structure is as follows:

FORMULA 5

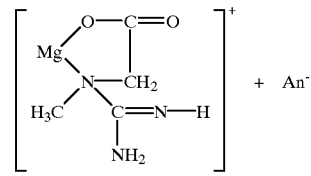

In the above depiction, the ligand to metal molar ratio is 1:1 and An⁻ may be any of a number of possible corresponding anions such as chloride (Cl⁻), iodide (I⁻), bisulfate (HSO₄⁻), bicarbonate (HCO₃⁻), dihydrogen phosphate (H₂PO₄⁻), phosphate (PO₄⁻), sulfate (SO₄²⁻), citrate, acetate (C₂H₃O₂⁻), lactate, malate, aminobutyrate, aspartate and glutamate or anions from other soluble salts. If the ligand to metal molar ratio is more than 1:1, then another creatinate anion may be present.

Specifically, magnesium creatine having a 1:1 molar ratio may be prepared by admixing equal moles of creatine and magnesium oxide in a citric acid solution. This produces a magnesium creatine chelate having a pH of about 8 to 9. To this, phosphoric acid is added to lower the pH level to about 7.

As discussed above, 2:1 structures of creatine chelates may also be formed. As such, another possible structure for magnesium creatine may be as follows:

FORMULA 6

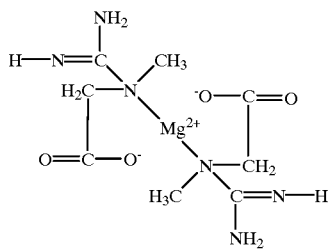

In the above depiction, the ligand to metal molar ratio is 2:1. However, this molecule is not fully coordinated as the carboxyl oxygen groups have not formed coordinate covalent bonds with the magnesium center. In fact, 2 coordination sites remain available, as represented by Mg²⁺, at the center. However, the available electrons of the carboxylate ion essentially neutralize the positive charge of the Mg²⁺ ion effectively resulting in a neutralized Mg ion. Full coordination is not required in the context of the present invention. The present invention contemplates chelates having a ligand to metal molar ratio from about 1:1 to 3:1 comprised of a heterocyclic creatine ring having a metal ion acting as the closing member. Therefore, the present invention is intended to cover chelates having coordinate covalent bonds at both the amine group and the carboxyl group and chelates having a coordinate covalent bond at the amine group and an ionic bond or other attraction at the carboxyl group. As such, under the right conditions, a fully coordinated magnesium creatine chelates may also be formed as depicted below:

FORMULA 7

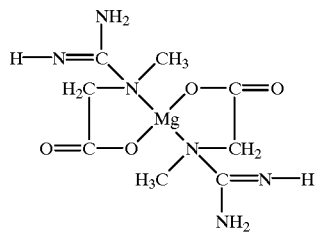

The present invention is also drawn toward a method of administering a creatine chelate to a warm-blooded mammal. The steps include 1) formulating an effective amount of creatine chelate into a nutritional supplement suitable for oral consumption; and 2) administering the nutritional supplement containing the creatine chelate to a warm blooded mammal. The nutritional supplement may be in the form of tablets, food bars, drinks, dry drink mixes or other substances acceptable for oral consumption. Tablets may be chewable or non-chewable. Food bars may be in the form of energy bars, weight loss bars, snack bars, granola bars or combinations thereof. Drinks may be in the form of energy drinks, sports drinks, fruit drinks, citrus drinks, carbonated drinks, other suitable drink mediums or combinations thereof. Finally, the dry drink mixes may be in the form of a fruit mix and/or citrus mix or other particulate drink mixes.

The following examples illustrate compositions and methods of preparing creatine chelates as well as various applications for which creatine chelates may be used. The following examples should not be considered as limitations of the present invention, but should merely teach how to make the best known creatine chelates based upon current experimental data.

EXAMPLES

Example 1

Preparation of Magnesium Creatine

Magnesium creatine chelate having a 1:1 ligand to metal molar ratio is prepared, first, by combining the following ingredients: 136.00 ml of water at 50 to 55° C.; 50.78 g of creatine monohydrate; 14.26 g of magnesium oxide; 7.63 g of 85% o-phosphoric acid; and 35.97 g of citric acid. The reaction mixture is heated to about 50 to 55° C. and spray dried. The expected yield of the dried product is 100.00 g when adjustments are made to account for evaporation of the water formed from the acid base reaction with magnesium oxide, waters of hydration associated with creatine monohydrate and 15% water associated with phosphoric acid. The assumption is made that 5.00 ml of water from the starting material is retained in the spray drying process.

The citric acid is used in the formulation as a source of acidic H⁺ ions so as to react with OH⁻ ions forming water and shifting the equilibrium Mg(OH)₂<—>Mg²⁺+2OH⁻ to the right. This presents the magnesium to the creatine ligand as soluble Mg²⁺ ions so that reaction can occur between the creatine and magnesium. The advantage of avoiding undesirable anions such as sulfate or chloride is realized by this process. Additionally, the soluble magnesium citrate initially formed has the advantage of having a higher overall pH than magnesium chloride or sulfate. This is of importance because hydrogen ions compete with metal ions for the lone pair of electrons on the amine groups. Phosphoric acid is used to bring the overall product pH down to a range that is desirable for greater food compatibility while not significantly adding to the overall weight of the finished product, and thus lowering the overall weight percent of magnesium and creatine in the product. Additionally, it has nutritive benefits and lacks the undesirable qualities associated chlorides and sulfates.

Example 2

Magnesium Creatine Fortified Energy Bars

The following formulations for three different energy bars show products with 200 mg of magnesium and 1.3 grams of creatine per 50 g using magnesium creatine prepared as discussed herein.

Ingredients for Milk Chocolate Peanut Butter Bar
8% Mg creatine chelate
13% soy protein isolate
8% whey powder
5% 10 D.E. maltodextrin
12% crystalline fructose
10% sucrose
2% nonfat dry milk 13% corn syrup 42 D.E.
2% peanut flour
6% peanut butter
4% partially hydrogenated soybean oil
2% honey
5% densified crisp rice #110
0.1% salt
0.5% lecithin
0.6% vitamin & mineral blend
0.4% butter vanilla flavor
0.4% natural flavor blend
8% water Ingredients for Black & White Chocolate Bar
8% Mg creatine chelate
13% soy protein isolate
8% whey powder
8% 10 D.E. maltodextrin
13% crystalline fructose
10% sucrose
3% nonfat dry milk
13% corn syrup 42 D.E.
5% dark cocoa
4% partially hydrogenated soybean oil
2% honey
5% densified crisp rice
0.1% salt
0.5% lecithin
0.6% vitamin & mineral blend
0.4% butter vanilla flavor
0.4% natural flavor blend
6% water Ingredients for DBL Dark Chocolate Crunch Bar
8% Mg creatine chelate
13% soy protein isolate
8% whey powder
6% 10 D.E. maltodextrin
15% crystalline fructose
10% sucrose
3% nonfat dry milk
13% corn syrup 42 D.E.
5% dark cocoa
4% partially hydrogenated soybean oil
2% honey
5% densified crisp rice
0.1% salt
0.5% lecithin
0.6% vitamin & mineral blend
0.4% butter vanilla flavor
0.4% natural flavor blend
6% water The general procedure for preparing these energy bars is as follows: First, in a blend tank, a slurry of water, corn syrup, sucrose, fructose, soybean oil and honey is formed. To this slurry, either peanut butter (milk chocolate peanut butter bar) or dark cocoa (black and white chocolate bar or DBL dark chocolate bar) is added. The slurry is then heated up to 120° F. and placed in a dough mixer. Other dry ingredients are then added to the slurry and the batch is mixed until homogenous. Next, flavors and crisp rice are added and mixed until dispersed.

The resulting mass is then loaded into an extruder and extruded to a predetermined size. The extruded bars are then run under refrigerated air blast to cool. Once cooled, the bars are coated with milk chocolate (milk chocolate peanut butter bar), white chocolate (black and white chocolate bar) or dark chocolate containing crisp rice (DBL dark chocolate crunch bar). The weight ratio of chocolate coating to extruded center is 1:2 (or 50 pounds of chocolate coating to 100 pounds of extruded center).

Example 3
Magnesium Creatine Fortified Energy Drink

This model formulation for an energy drink will provide a product with 200 mg of magnesium and 1.3 g of creatine per 8-fl oz. using magnesium creatine as disclosed herein.

Ingredients for Vanilla Flavored Drink
1.1% Mg creatine chelate
4% 10 D.E. maltodextrin
9% sucrose
8% nonfat dry milk
0.25% sodium citrate
0.02% carrageenan
0.6% vitamin & mineral blend
0.55% vanilla flavor
76.3% filtered water A liquid drink is prepared as sucrose, nonfat dry milk, maltodextrin, sodium citrate, carrageenan, vitamins and minerals and magnesium creatine are blended into water under good agitation. To this liquid, vanilla flavor is added and the complete mixture is heat treated to 165° F. and homogenized. The product is cooled to 40° F. and packaged.

A powdered drink is prepared as all dry ingredients are blended together as a premix for mixing with water or milk.

Example 4
Magnesium Creatine Fortified Sports Drink

This formulation for a sports drink will provide a product with 300 mg of magnesium and 1.9 g of creatine per 8-fl oz. using magnesium creatine as disclosed herein.

Ingredients for Fruit Punch Flavored Sports Drink
1.65% Mg creatine chelate
2.7% 42 D.E. corn syrup
3.5% sucrose
0.3% citric acid
0.1% salt
0.5% fruit punch flavor
91.25% filtered water A liquid drink is prepared as sugar, corn syrup citric acid, salt and magnesium creatine is blended into water under good agitation. To this liquid, a fruit punch flavoring is added.

The complete batch is heat treated to 150° F., allowed to cool to 40° F. and packaged.

Example 5
Preparation of Calcium Creatine

Calcium creatine chelate having a 1:1 ligand to metal molar ratio is prepared, first, by combining the following ingredients: 540.00 ml of water at 50 to 55° C.; 150.00 g of creatine monohydrate; 59.98 g of calcium oxide; and 23.43 g of 85% o-phosphoric acid. The reaction mixture is heated to about 50 to 55° C. and spray dried. The expected yield of the dried product is 314.49 g when adjustments are made to account for evaporation of the water formed from the acid base reaction with calcium oxide, waters of hydration associated with creatine monohydrate and 15% water associated with phosphoric acid. The assumption is made that 15.72 ml of water from the starting material is retained in the spray drying process.

Example 6
Calcium Creatine Fortified Energy Bar

The following formulation for a black and white chocolate energy bar provides a product with 500 mg of calcium and 2 grams of creatine per 50 g using calcium creatine prepared as discussed herein.

Ingredients for Black & White Chocolate Bar
12% Ca creatine chelate
13% soy protein isolate
8% whey powder
6% 10 D.E. maltodextrin
11% crystalline fructose
10% sucrose
3% nonfat dry milk
13% corn syrup 42 D.E.
5% dark cocoa
4% partially hydrogenated soybean oil
2% honey
5% densified crisp rice
0.1% salt
0.5% lecithin
0.6% vitamin & mineral blend
0.4% vanilla flavor
0.4% natural flavor blend
6% water The procedure for preparing the black and white energy bar is as follows: First, in a blend tank, a slurry of water, corn syrup, sucrose, fructose, soybean oil and honey is formed. The slurry is heated up to 120° F. and placed in a dough mixer where the other ingredients are added and mixed until homogenous. Next, flavors and crisp rice are added and mixed until dispersed. The resulting mass is then loaded into an extruder and extruded to a predetermined size. The extruded bars are then run under refrigerated air blast to cool. Once cooled, the bars are coated with white chocolate. The weight ratio of chocolate coating to extruded center is 1:2 (or 50 pounds of chocolate coating to 100 pounds of extruded center). Once tempered, the finished bar may be packaged.

Example 7
Preparation of Zinc Creatine

Zinc creatine chelate having a 1:1 ligand to metal molar ratio is prepared, first, by combining the following ingredients: 620.48 ml of water at 50 to 55° C.; 150.00 g of creatine monohydrate; 83.85 g of zinc oxide; 17.80 g of 85% o-phosphoric acid; and 106.26 g of citric acid. The reaction mixture is heated to about 50 to 55° C. and spray dried. The expected yield of the dried product is 335.32 g when adjustments are made to account for evaporation of the water formed from the acid base reaction with zinc oxide, waters of hydration associated with creatine monohydrate and 15% water associated with phosphoric acid. The assumption is made that 18.12 ml of water from the starting material is retained in the spray drying process.

Example 8
Zinc Creatine Fortified Sports Drink

This formulation for a sports drink will provide a product with 5 mg of zinc and 1.9 g of creatine per 8-fl oz. using zinc creatine as disclosed herein.

Ingredients for Fruit Punch Flavored Sports Drink
0.12% Zn creatine chelate
5% 42 D.E. corn syrup
0.85% creatine monohydrate
8% sucrose
0.5% citric acid
0.1% salt
0.5% fruit punch flavor
84.93% filtered water A liquid drink is prepared as sugar, corn syrup, citric acid, salt, zinc monohydrate and zinc creatine is blended into water under good agitation. To this liquid, a fruit punch flavoring is added. The complete batch is heat treated to 150° F., allowed to cool to 40° F. and packaged.

While the invention has been described with reference to certain preferred embodiments, those skilled in the art will appreciate that various modifications, changes, omissions, and substitutions can be made without departing from the spirit of the invention. For example, the creatine chelates of the present invention may be used to fortify other foods and/or drinks such as weight loss bars, chewable tablets, etc. Further, creatine chelates having other chelated metals than those in Examples 1, 5 and 7 may be prepared by following similar procedures as would be apparent to those skilled in the art. It is intended, therefore, that the invention be limited only by the scope of the following claims.

We claim:

1. A creatine chelate comprised of a creatine ligand bonded to a metal selected from the group consisting of Mg, Ca, Cu, Zn, Fe, Cr, Co, Mo, Se and Mn to form a chelate ring, and wherein said ligand to metal molar ratio is from 1:1 to 3:1.

2. A creatine chelate as in claim 1 wherein said creatine ligand is provided by a member selected from the group consisting of creatine, creatine salts, creatine esters, creatine amides, creatine hydrates and combinations thereof.

3. A creatine chelate as in claim 2 wherein said metal is provided by a member selected from the group consisting of ions, elemental, oxides, hydroxides, carbonates, bicarbonates, sulfates, nitrates, chlorides, phosphates, citrates, lactates, amino acid salts and combinations thereof.

4. A creatine chelate as in claim 1 wherein said creatine chelate is defined by the formula:

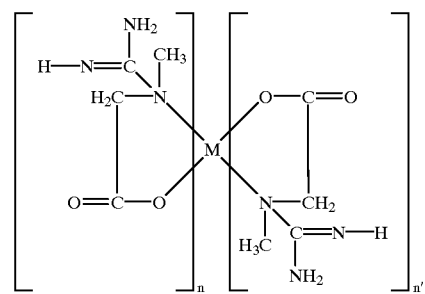

wherein M is a metal selected from the group consisting of Mg, Ca, Cu, Zn, Fe, Cr, Co, Mo, Se and Mn, and wherein n is 1 and n' is 0, 1, or 2.

5. A creatine chelate as in claim 4 wherein M is Mg.
6. A creatine chelate as in claim 5 wherein n' is 0.
7. A creatine chelate as in claim 5 wherein n' is 1.
8. A creatine chelate as in claim 4 wherein M is Ca.
9. A creatine chelate as in claim 8 wherein n' is 0.
10. A creatine chelate as in claim 4 wherein M is Zn.
11. A creatine chelate as in claim 10 wherein n' is 0.
12. A creatine chelate as in claim 4 wherein M is Cr.
13. A creatine chelate as in claim 12 wherein n' is 0.
14. A creatine chelate as in claim 12 wherein n' is 1.
15. A creatine chelate as in claim 12 wherein n' is 2.
16. A creatine chelate as in claim 4 wherein M is Mn.
17. A creatine chelate as in claim 16 wherein n' is 0.
18. A creatine chelate as in claim 4 wherein M is Fe.
19. A creatine chelate as in claim 18 wherein n' is 0.
20. A creatine chelate as in claim 18 wherein n' is 1.
21. A creatine chelate as in claim 18 wherein n' is 2.
22. A method of preparing a creatine chelate comprising reacting creatine with a metal selected from the group consisting of Mg, Ca, Cu, Zn, Fe, Cr, Co, Mo, Se and Mn in an aqueous solution, and wherein said creatine to metal molar ratio is from about 1:1 to 3:1.

23. A method according to claim 22 wherein said creatine is provided by the group consisting of creatine, creatine salts, creatine esters, creatine amides, creatine hydrates and combinations thereof.

24. A method according to claim 23 wherein said metal is provided by the group consisting of ions, elemental, oxides, hydroxides, carbonates, bicarbonates, sulfates, nitrates, chlorides, phosphates, citrates, lactates, amino acid salts and combinations thereof.

25. A method according to claim 24 wherein said aqueous solution is water or an acidified aqueous solution selected from the group consisting of citric, phosphoric, sulfuric, hydrochloric, aminobutyric, malic, acetic, tartaric, maleic, lactic and naturally occurring amino acids.

26. A method according to claim 22 wherein said metal is Mg.

27. A method according to claim 26 wherein said creatine to Mg molar ratio is 1:1.

28. A method according to claim 26 wherein said creatine to Mg molar ratio is 2:1.

29. A method according to claim 22 wherein said metal is Ca.

30. A method according to claim 29 wherein said creatine to Ca molar ratio is 1:1.

31. A method according to claim 22 wherein said metal is Zn.

32. A method according to claim 31 wherein said creatine to Zn molar ratio is 1:1.

33. A method according to claim 22 wherein said metal is Cr.

34. A method according to claim 33 wherein said creatine to Cr molar ratio is 1:1.

35. A method according to claim 33 wherein said creatine to Cr molar ratio is 2:1.

36. A method according to claim 33 wherein said creatine to Cr molar ratio is 3:1.

37. A method according to claim 22 wherein said metal is Mn.

38. A method according to claim 37 wherein said creatine to Mn molar ratio is 1:1.

39. A method according to claim 22 wherein said metal is Fe.

40. A method according to claim 39 wherein said creatine to Fe molar ratio is 1:1.

41. A method according to claim 39 wherein said creatine to Fe molar ratio is 2:1.

42. A method according to claim 39 wherein said creatine to Fe molar ratio is 3:1.

43. A method according to claim 26 wherein said Mg is provided by magnesium oxide.

44. A method according to claim 23 wherein said creatine is provided by creatine monohydrate.

45. A method according to claim 25 wherein said aqueous solution is citric acid.

46. A method according to claim 22 wherein subsequent to said admixing step, a pH adjuster is added selected from the group consisting of o-phosphoric acid, citric, malic, acetic, hydrochloric, tartaric, lactic, nitric, sulfuric and naturally occurring amino acids.

47. A method according to claim 46 wherein said pH adjuster is o-phosphoric acid.

48. A method according to claim 46 wherein said pH adjuster is added to reduce the pH from about 7.5–10 to about 7.

49. A method of administering a creatine chelate to a warm-blooded mammal comprising the steps of:

formulating an effective amount of said creatine chelate into a nutritional supplement suitable for oral consumption; and administering said nutritional supplement containing said creatine chelate to a warm blooded mammal.

50. A method as in claim 49 wherein said nutritional supplement is selected from the group consisting of tablets, food bars, drinks and dry drink mixes.

51. A method as in claim 50 wherein said nutritional supplement is a chewable or non-chewable tablet.

52. A method as in claim 50 wherein said nutritional supplement is a food bar selected from the group consisting of energy bars, weight loss bars, snack bars, granola bars and combinations thereof.

53. A method as in claim 50 wherein said nutritional supplement is a drink selected from the group consisting of energy drinks, sports drinks, citrus drinks, fruit drinks, carbonated drinks and combinations thereof.

54. A method as in claim 50 wherein said nutritional supplement is a dry drink mix selected from the group consisting of fruit mix, citrus mix and combinations thereof.

* * * * *